United States Patent
Kozmin et al.

(10) Patent No.: US 7,569,594 B2
(45) Date of Patent: Aug. 4, 2009

(54) ANALOGS OF LEUCASCANDROLIDE A

(75) Inventors: Sergey A. Kozmin, Chicago, IL (US); Jelena Janjic, Chicago, IL (US)

(73) Assignee: The University of Chicago, Chicago, IL (US)

( * ) Notice: Subject to any disclaimer, the term of this patent is extended or adjusted under 35 U.S.C. 154(b) by 478 days.

(21) Appl. No.: 11/348,839

(22) Filed: Feb. 7, 2006

(65) Prior Publication Data

US 2006/0178355 A1 Aug. 10, 2006

Related U.S. Application Data

(60) Provisional application No. 60/650,987, filed on Feb. 7, 2005.

(51) Int. Cl.
*A61K 31/422* (2006.01)
*A61K 31/351* (2006.01)
*C07D 263/30* (2006.01)
*C07D 315/00* (2006.01)

(52) U.S. Cl. .................. 514/374; 514/451; 548/235; 548/255; 549/415

(58) Field of Classification Search ............ 514/374, 514/451; 548/235, 255; 549/415
See application file for complete search history.

(56) References Cited

OTHER PUBLICATIONS

D'Ambrosio et al. "6. *Leucascandrolide A, a New Type of Macrolide: the First Powerfully Bioactive Metabolite of Calcareous Sponges*", Helv. Chim. Acta—vol. 79 (1996), pp. 51-60.
Hornberger et al., "*Total Synthesis of Leucascandrolide A*", J. Am. Chem. Soc. 2000, 122, pp. 12894-12895.
Crimmins et al., "*Synthesis of the C1-C13 Fragment of Leucasscandrolide A*", Org. Lett., 2000, vol. 2, No. 5, pp. 597-599.
Vakalopoulos et al., "*Versatile 8-Oxabicyclo[3.2.1]oct-6-en-3-one: Stereoselective Methodology for Generating C-Glycosides, δ-Valerolactones, and Polyacetate Segments*", Org. Lett., 2001, vol. 3, No. 2, pp. 177-180.
Kozmin et al., "*Efficient Stereochemical Relay en Route to Leucascandrolide A*", Org. Lett. 2001, vol. 3, No. 5, pp. 755-758.
Wang et al., "*Synthesis of Leucascandrolide A via a Spontaneous Macrolactolization*", J. Am. Chem. Soc. 2002, vol. 124, No. 46, pp. 13670-13671.
Wang et al., "*Synthesis of Leucascandrolide A*", Pure Appl. Chem., vol. 77, No. 7, 2005, pp. 1161-1169.
Kozmin et al., PowerPoint presentation entitled "*Leucascandrolide A: Using Synthesis to Understand Structure-Activity Profile*", dated Mar. 25, 2003, 21 pages.

*Primary Examiner*—Kamal A Saeed
*Assistant Examiner*—Samantha L Shterengarts
(74) *Attorney, Agent, or Firm*—Brinks Hofer Gilson & Lione

(57) ABSTRACT

The present invention describes leucascandrolide analogs of the formula (I), intermediates of the formula (III), pharmaceutical compositions containing the same, methods for preventing cell proliferation, and methods for treating cancers and other proliferative diseases.

18 Claims, No Drawings

ANALOGS OF LEUCASCANDROLIDE A

RELATED APPLICATIONS

This application claims the priority benefit to provisional application U.S. Ser. No. 60/650,987, filed Feb. 7, 2005; which is incorporated by reference in its entirety.

FEDERALLY SPONSORED RESEARCH OR DEVELOPMENT

This invention was made with government support under R01 CA93457 awarded by the NIH. The government has certain rights in the invention.

BACKGROUND OF THE INVENTION

Leucascandrolide A is a highly cytotoxic macrolide isolated from the calcareous sponge Leucascandra caveolata. This compound exhibits a highly potent cell growth inhibitory activity in human A549 non-small lung caner cells (GI50=0.93 nM) and HCT-116 colon cancer cells (GI50=0.87 nM). Further, leucascandrolide A proves to be an effective fungistatic inhibitor in a W303 strain of yeast *S. cerevisiae* as well (33 mm/11.2 mg inhibition diameter per disk).

The total synthesis of leucascandrolide A has been achieved by several groups: D'Ambrosio et al., *Helv. Chim. Acta*, 1996, 79: 51-60; Hornberger et al., *J. Am. Chem. Soc.*, 2000, 122:12894-95; Crimmins et al., *Org. Lett.*, 2000, 2:597-99; Vakalopoulos et al., *Org. Lett.*, 2001, 3, 177-180; Kozmin, *Org. Lett.*, 2001, 3:755-58; Yang et al., *Pure Appl. Chem.*, 2005, 77:1161-69; Yang et al., *J. Am. Chem. Soc.*, 2002, 124: 13670-71.

Because of its extraordinary ability to inhibit both human cancer cell proliferation and yeast growth, leucascandrolide A is a potential candidate in cancer treatment. However, the complicated synthesis of leucascandrolide A remains a challenge. Access to less draconian methods for preparing this target molecule and its simplified analogs, by developing highly efficient synthesis routes for these compounds, is thus a crucial step forward in efforts to determine the mode of action of this compound in yeast and mammalian cells, and to reveal any structure-activity relationship. Such methods and synthetic analogs and intermediates are provided herein.

BRIEF SUMMARY OF THE INVENTION

The present invention describes leucascandrolide analogs of the formula (I), intermediates of the formula (III), pharmaceutical compositions containing the same, methods for preventing cell proliferation, and methods for treating cancers and other proliferative diseases.

DETAILED DESCRIPTION OF THE INVENTION

Abbreviations and Definitions

When describing the compounds, compositions, methods and processes of this invention, the following terms have the following meanings, unless otherwise indicated.

"Affinity label" as used herein refers to a label which is specifically trapped by a complementary ligand. Exemplary labels include proteins or amino acids. Suitable complementary ligands include antibodies, metals, etc. Either of the label or complementary label can be attached to compound (I). Examples of pairs of affinity marker/affinity ligand include but are not limited to: Maltose-Binding Protein (MBP)/maltose; Glutathione S Transferase (GST)/glutathione; histidine (His)/metal. The metal used as affinity ligand may be selected from the group consisting of: cobalt, zinc, copper, iron, and nickel (Wong et al. (1991), *Separation and Purification Methods*, 20(1), 49-106). Preferably, the metal selected is nickel. The affinity ligand can be set up in columns to facilitate separation by affinity chromatography.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, thioalkyl, aminoalkyl, and the like.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Aryl" refers to a polyunsaturated, aromatic hydrocarbon group having a single ring (monocyclic) or multiple rings (preferably bicyclic) which can be fused together or linked covalently. Aryl groups with 6-10 carbon atoms are preferred. Examples of aryl groups include phenyl and naphthalene-1-yl, naphthalene-2-yl, biphenyl and the like. Aryl groups can be substituted or unsubstituted, unless otherwise indicated.

"Halo" or "halogen", by itself or as part of a substituent refers to a chlorine, bromine, iodine, or fluorine atom. Additionally, "haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic group containing at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

Exemplary heterocyclic groups may be represented by formula (A) below:

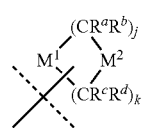

(A)

where formula (A) is attached via a free valence on either $CR^aR^b$, $CR^cR^d$, $M^1$ or $M^2$;

$M^1$ represents O, $NR^e$, or $S(O)_l$;

$M^2$ represents $CR^fR^g$, O, $S(O)_l$, or $NR^e$;

l is 0, 1 or 2;

j is 1, 2 or 3;

k is 1, 2 or 3, with the proviso that j+k is 3, 4, or 5; and $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, —COR, —CO$_2$R, —C(O)NRR, —NRCOR, —S(O)$_2$R, —S(O)$_2$NRR, —NS(O)$_2$RR, —NRR, —OR, —VCOR, —VCO$_2$R, —VC(O)NRR, —VNRCOR, —VS(O)$_2$R, —VS(O)$_2$NRR, —VNS(O)$_2$RR, —VNRR, and —VOR, where V is a member selected from the group consisting of $C_{1-4}$ alkylene, $C_{2-4}$ alkenylene and $C_{2-4}$ alkynylene; and each R is independently hydrogen or $C_{1-6}$ alkyl, and where the aliphatic portions of each of the $R^a$, $R^b$, $R^c$, $R_d$, $R^e$, $R^f$, and $R^g$ substituents are optionally substituted with from one to three members selected from the group consisting of halogen, —OR, —OC(O)NRR, —SR, —S(O)R, —S(O)$_2$R, —S(O)$_2$NRR, —NRS(O)$_2$R, —C(O)NRR, —C(O)R, —NRC(O)R, —NRC(O)NRR, —CO$_2$R, —NRCO$_2$R, —CN, —NO$_2$, —NRR, —NRS(O)NRR and —NRS(O)$_2$NRR, where each R is independently hydrogen or an unsubstituted $C_{1-6}$ alkyl. Additionally, any two of $R^a$, $R^b$, $R^c$, $R^d$, $R^e$, $R^f$, and $R^g$ may be combined to form a bridged or spirocyclic ring system.

Preferably, the number of $R^a+R^b+R^c+R^d$ groups that are other than hydrogen is 0, 1 or 2. More preferably, $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, —C(O)R, —CO$_2$R, —C(O)NRR, —NRC(O)R, —S(O)$_2$R, —S(O)$_2$NRR, —NS(O)$_2$RR, —NRR, and —OR, where each R is independently hydrogen or unsubstituted $C_{1-8}$ alkyl; and where the aliphatic portions of each of the $R^a$, $R^b$, $R^c$, $R^d$, $R^e$, $R^f$, and $R^g$ substituents are optionally substituted with from one to three members selected from the group consisting of halogen, —OR, —OC(O)NRR, —SR, —S(O)R, —S(O)$_2$R, —S(O)$_2$NRR, —NRS(O)$_2$R, —C(O)NRR, —C(O)R, —NRC(O)R, —NRC(O)NRR, —CO$_2$R, —NRCO$_2$R, —CN, —NO$_2$, —NRR, —NRS(O)NRR and —NRS(O)$_2$NRR, where each R is independently hydrogen or an unsubstituted $C_{1-6}$ alkyl.

More preferably, $R^a$, $R^b$, $R^c$, $R^d$, $R^e$, $R^f$, and $R^g$ are independently hydrogen or $C_{1-4}$alkyl. In another preferred embodiment, at least three of $R^a$, $R^b$, $R^c$, $R^d$, $R^e$, $R^f$, and $R^g$ are hydrogen.

"Hydroxy-protecting group" refers to a substituent of a hydroxy group that blocks or protects the hydroxy functionality. Suitable protecting groups include $C_{1-6}$ alkyl group (e.g., methyl group, ethyl group, and the like), phenyl-$C_{1-6}$ alkyl group (e.g., benzyl group, and the like), $C_{1-6}$ alkyl-carbonyl group (e.g., acetyl group, and the like), benzoyl group, alkyl-substituted silyl group (e.g., trimethylsilyl group, tert-butyldimethylsilyl group, and the like).

"Heteroaryl" refers to an aromatic group containing at least one heteroatom. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is =O, the resulting group may have either a carbonyl (—C(O)—) or a N-oxide (—N$^+$—O$^-$) or —S(O)— or —S(O)$_2$—.

Suitable substituents for substituted alkyl, substituted alkenyl, and substituted alkynyl include halogen, —CN, —CO$_2$R', —C(O)R', —C(O)NR'R'', oxo (=O or —O$^-$), —OR', —OC(O)R', —OC(O)NR'R''—NO$_2$, —NR'C(O)R'', —NR'''C(O)NR'R'', —NR'R'', —NR'CO$_2$R'', —NR'S(O)$_2$R''', —SR', —S(O)R', —S(O)$_2$R', —S(O)$_2$NR'R'', —SiR'R''R''', —N$_3$, substituted or unsubstituted $C_{6-10}$ aryl, substituted or unsubstituted 5- to 10-membered heteroaryl, and substituted or unsubstituted 3-to 10-membered heterocyclyl, in a number ranging from zero to (2m'+1), where m' is the total number of carbon atoms in such radical.

Suitable substituents for substituted aryl, substituted heteroaryl and substituted heterocyclyl include halogen, —CN, —CO$_2$R', —C(O)R', —C(O)NR'R'', oxo (=O or —O$^-$), —OR', —OC(O)R', —OC(O)NR'R'', —NO$_2$, —NR'C(O)R'', —NR'''C(O)NR'R'', —NR'R'', —NR'CO$_2$R'', —NR'S(O)$_2$R''', —SR', —S(O)R', —S(O)$_2$R', —S(O)$_2$NR'R'', —NR'—C(NHR'')=NR''', —SiR'R''R''', —N$_3$, substituted or unsubstituted $C_{1-8}$ alkyl group, substituted or unsubstituted $C_{6-10}$ aryl group, substituted or unsubstituted 5- to 10-membered heteroaryl, and substituted or unsubstituted 3- to 10-membered heterocyclyl, in a number ranging from zero to the total number of open valences on the aromatic ring system.

As used above, R', R'' and R''' each independently refer to a variety of groups including hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, substituted or unsubstituted arylalkyl, and substituted or unsubstituted aryloxyalkyl. When R' and R'' are attached to the same nitrogen atom, they can be combined with the nitrogen atom to form a 3-, 4-, 5-, 6-, or 7-membered ring (for example, —NR'R'' includes 1-pyrrolidinyl and 4-morpholinyl).

Two of the substituents on adjacent atoms of an aryl or heteroaryl ring may optionally be replaced with a substituent of the formula -T-C(O)—(CH$_2$)$_q$—U— where T and U are independently —NR$^i$—, —O—, —CH$_2$— or a single bond, and q is an integer of from 0 to 2. Alternatively, two of the substituents on adjacent atoms of the aryl or heteroaryl ring may optionally be replaced with a substituent of the formula -A'-(CH$_2$)$_r$—B'—, where A' and B' are independently —CH$_2$—, —O—, —NR$^i$—, —S—, —S(O)—, —S(O)$_2$—, —S(O)$_2$NR$^i$— or a single bond, and r is an integer from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^i$—, —S—, —S(O)—, —S(O)$_2$—, or —S(O)$_2$NR$^i$—. The substituent R$^i$ in —NR$^i$— and —S(O)$_2$NR$^i$— is hydrogen or unsubstituted C$_{1-6}$alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M., et al, "Pharmaceutical Salts", *J. Pharmaceutical Science,* 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

"Therapeutically effective amount" means the amount of the subject compound that will elicit the biological or medical response of a cell, tissue, system, or animal, such as a human, that is being sought by the researcher, veterinarian, medical doctor or other treatment provider.

"Treating" or "treatment" as used herein refers to the treating or treatment of a disease or medical condition (such as a bacterial infection) in a patient, such as a mammal (particularly a human or a companion animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

COMPOUNDS OF THE PRESENT INVENTION

A compound of the formula (I) or a salt, enantiomer or racemate thereof:

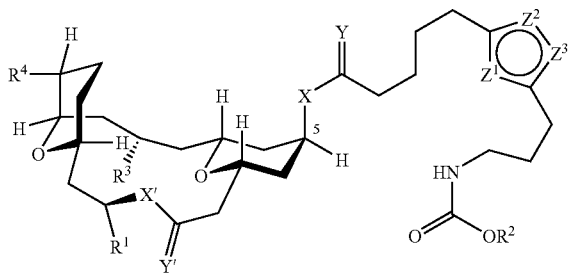

wherein $R^1$ is —$(C_{0-15}$alkylene)-L-$(C_{0-15}$ alkylene)-$Z^4$, where each alkylene group in $R^1$ independently contains from 0 to 3 double or triple bonds; and wherein each alkylene group of $R^1$ may be unsubstituted or substituted; L is a bond, substituted or unsubstituted heterocyclyl, substituted or unsubstituted aryl, substituted or unsubstituted heteroaryl, —$(CH_2CH_2O)_a$—, —$CONR^i$—, —$NR^iCO$—, —$C(O)$—, —S—, —$S(O)$— or —$S(O)_2$—; $Z^4$ is hydrogen, —$NR^iR^{vi}$, —$OR^{vi}$, —$SR^{vi}$, or —$CONR^iR^{vi}$;

$R^2$ is $C_{1-3}$ alkyl;

$R^3$ is hydrogen, $C_{1-6}$ alkyl, —$OR^i$, —$SR^i$, or —$O(CO)R^i$;

$R^4$ is hydrogen or $C_{1-6}$ alkyl;

each X and X' are independently O or $NR^i$;

each Y and Y' are independently O or S;

each of $Z^1$, $Z^2$, and $Z^3$, is independently selected from $CR^i$, N, O or S;

the alkylene groups within the substituent on C5 may independently contain from 1 to 2 double bonds;

a is an integer from 1-10;

each $R^i$ and $R^{ii}$ are independently hydrogen or $C_{1-6}$ alkyl; and $R^{vi}$ is hydrogen, $C_{1-6}$ alkyl, or a label;

provided that if X, X', Y, and Y' are O, $R^2$ is methyl, $R^3$ is methyl, and $R^4$ is methyl or hydrogen, then $R^1$ is not —CH=CHCH$_2$CH(CH$_3$)$_2$, CH$_2$CH$_2$CH$_2$CH(CH$_3$)$_2$, C≡CCH$_2$CH(CH$_3$)$_2$, —CH$_3$ or —H.

In a first embodiment, the alkylene groups in $R^1$ independently contain at least one carbon atom, preferably 3-10 carbon atoms. In another embodiment, the alkylene groups in $R^1$ contain no double or triple bonds. In another embodiment, the alkylene groups in $R^1$ contain at least 1 double or triple bond, preferably at least 1 triple bond. The alkylene groups in $R^1$ can be unsubstituted or substituted with 1-3 subsituents selected from the group consisting of 1 to 3 substituents selected from alkyl, halogen, —$NR^iR^{ii}$, —$OR^i$, —$SR^i$, —CN, —$NO_2$, =O, —$OC(O)R^i$, —$C(O)R^i$, —$C(O)NR^iR^{ii}$, —$OC(O)NR^iR^{ii}$, —$NR^{ii}C(O)R^i$, —$NR^iC(O)NR^{iii}R^{ii}$, —$CO_2R^i$, —$NR^iR^{ii}$, —$NR^{ii}CO_2R^i$, —$SR^i$, —$S(O)R^i$, —$S(O)_2R^i$, —$S(O)_2NR^iR^{ii}$, —$NR^iS(O)_2R^{ii}$, unsubstituted or substituted aryl, unsubstituted or substituted heteroaryl, and unsubstituted or substituted heterocyclyl, wherein $R^{iii}$ is hydrogen or $C_{1-6}$ alkyl. Preferred substituents include halogen and alkyl.

In a second embodiment, L is a bond. In another embodiment, L is a substituted or unsubstituted heterocyclyl, substituted or unsubstituted aryl, substituted or unsubstituted heteroaryl. When L is a heterocyclyl, aryl or heteroaryl, it preferably has 5-10 members. Suitable heterocyclyl, aryl or heteroaryl groups are described above under the definitions section. When substituted, L preferably contains 1-3 substituents selected from the group consisting of 1 to 3 substituents selected from alkyl, halogen, —$NR^iR^{ii}$, —$OR^i$, —$SR^i$, —CN, —$NO_2$, =O, —$OC(O)R^i$, —$C(O)R^i$, —$C(O)NR^iR^{ii}$, —$OC(O)NR^iR^{ii}$, —$NR^{ii}C(O)R^i$, —$NR^iC(O)NR^{iii}R^{ii}$, —$CO_2R^i$, —$NR^iR^{ii}$, —$NR^{ii}CO_2R^i$, —$SR^i$, —$S(O)R^i$, —$S(O)_2R^i$, —$S(O)_2NR^iR^{ii}$, —$NR^iS(O)_2R^{ii}$, unsubstituted or substituted aryl, unsubstituted or substituted heteroaryl, and unsubstituted or substituted heterocyclyl, wherein $R^{iii}$ is hydrogen or $C_{1-6}$ alkyl. Preferred substituents include halogen and alkyl.

In a third embodiment, $Z^4$ is —$NR^iR^{vi}$, —$OR^{vi}$, —$SR^{vi}$, or —$CONR^iR^{vi}$, preferably —$NR^iR^{vi}$, more preferably —$NHR^{vi}$. In another embodiment, $R^{vi}$ is a marker (such as affinity label or fluorescent marker), a small molecule (such as a therapeutic agent), or biological group (such as an antibody).

In a fourth embodiment, $R^1$ is —$C_{1-15}$ alkynyl; —$(C_{1-8}$ alkylene)-L-$(C_{1-6}$ alkylene)-$Z^4$; or —$(C_{1-8}$ alkylene)-L-$(C_{1-6}$ alkylene)-$NR^iR^{ii}$, where L is a unsubstituted or substituted 5- or 6-membered heterocyclyl, unsubstituted or substituted 5- or 6-membered heteroaryl, or unsubstituted or substituted phenyl.

In a fifth embodiment, the substituent at C5 contains 1 to 3 double bonds, preferably 2 double bonds. In a preferred embodiment, the compound is of the formula (II):

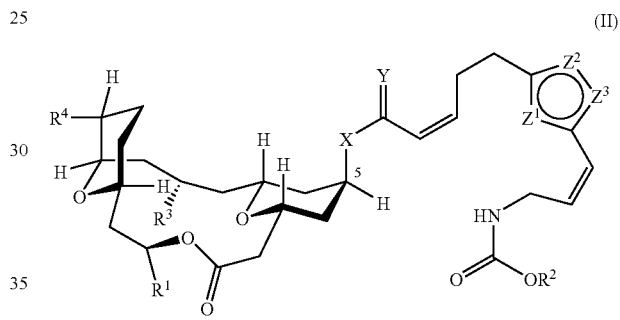

where $R^1$, $R^2$, $R^3$, $R^4$, $Z^1$, $Z^2$ and $Z^3$ are as described for formula (I).

In a sixth embodiment, at least one of $Z^1$, $Z^2$ and $Z^3$ is CH. In another embodiment, $Z^1$ is N, $Z^2$ is CH, and $Z^3$ is O.

In a seventh embodiment, X and X' are O.

In an eight embodiment, Y and Y' are O.

In a ninth embodiment, the compounds of the present invention have the first, second and third embodiments.

In a tenth embodiment, the compounds of the present invention have the fifth and ninth embodiments.

In an eleventh embodiment, the compounds of the present invention have the fourth and fifth embodiments.

In a twelfth embodiment, the compounds of the present invention have the sixth and ninth embodiments.

In a thirteenth embodiment, the compounds of the present invention have the fourth and sixth embodiments.

In a fourteenth embodiment, the compounds of the present invention have the seventh and ninth embodiments.

In a fifteenth embodiment, the compounds of the present invention have the fourth and seventh embodiments.

In a sixteenth embodiment, the compounds of the present invention have the eighth and ninth embodiments.

In a seventeenth embodiment, the compounds of the present invention have the fourth and eighth embodiments.

In a eighteenth embodiment, the compounds of the present invention have the fifth, seventh and eighth embodiments.

In a nineteenth embodiment, the compounds of the present invention have the fifth and sixth embodiments.

The present invention also relates to intermediates of the formula (III) or a salt, enantiomer or racemate thereof:

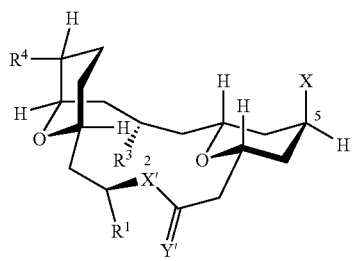

wherein $R^1$ is —($C_{0-15}$ alkylene)-L-($C_{0-15}$ alkylene)-$Z^4$
wherein each alkylene group in $R^1$ independently contains from 0 to 3 double or triple bonds; and wherein each alkylene group of $R^1$ may be unsubstituted or substituted;

L is a bond, substituted or unsubstituted heterocyclyl, substituted or unsubstituted aryl, substituted or unsubstituted heteroaryl, —$CONR^i$—, —$NR^iCO$—, —C(O)—, —S—, —S(O)— or —$S(O)_2$—;

$Z^4$ is hydrogen, —$NR^iR^{ii}$, —$OR^i$, —$SR^i$, or —$CONR^iR^{ii}$;

$R^3$ is hydrogen, $C_{1-6}$ alkyl, —$OR^i$, —$SR^i$, or —$O(CO)R^i$;

$R^4$ is hydrogen or $C_{1-6}$ alkyl;

X is $OR^{iii}$;

X' is O or $NR^i$;

Y' is O or S;

each $R^i$ and $R^{ii}$ are independently hydrogen or $C_{1-6}$ alkyl; and $R^{iii}$ is a hydroxy-protecting group, provided that if X, X', Y, and Y' are O, $R^2$ is methyl, $R^3$ is methyl, and $R^4$ is methyl or hydrogen, then $R^1$ is not —CH=CHCH$_2$CH(CH$_3$)$_2$, CH$_2$CH$_2$CH$_2$CH(CH$_3$)$_2$, C≡CCH$_2$CH(CH$_3$)$_2$, —CH$_3$ or —H.

Various embodiments of the intermediates (III) mirror those set fourth above for compounds (I). Preferred intermediates include:

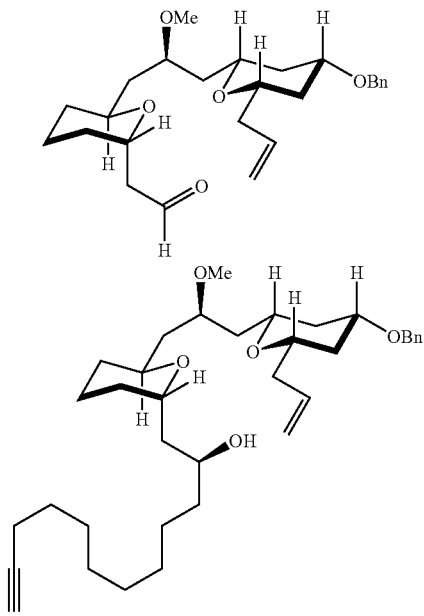

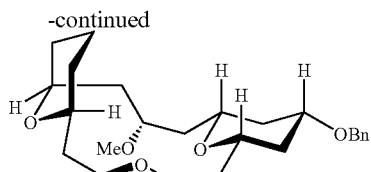

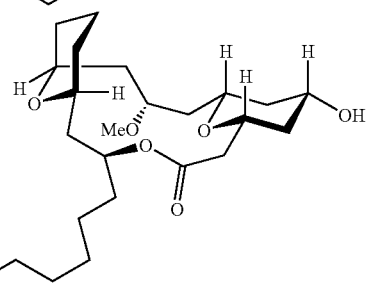

or a salt, enantiomer or racemate thereof.

The present invention also relates to compositions containing the compounds of the present invention (I) along with a pharmaceutical carrier.

Methods of Preventing Cell Proliferation and Treating Cancers

In yet another aspect, the present invention provides methods of preventing cell proliferation by administering a therapeutically effective amount of any compound of formula (I) above either in vitro (assays) or in vivo (treatment). In yet another aspect, the present invention provides methods of treating or preventing cancer by administering to a subject having such a condition or disease a therapeutically effective amount of any compound of formula (I) above. Compounds for use in the present methods include those compounds according to formula (I), those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The compounds of the present invention can be tested for anti-proliferative activity using one of the following cells lines: HCT116 (Colorectal carcinoma)(Kodach, *Carcinogenesis*. 2005 Dec. 12 Epub); PC3 (Prostate carcinoma)(Li et al., *Oncogene*. 2006 Jan. 26;25(4):525-35); H460 and A549 cells (Non small cell lung carcinoma)((Fan et al., *Bioorg. Med. Chem.*, 2006 Jan. 12; Janmaat et al., *Int. J. Cancer*. 2006 Jan. 1;118(1):209-14); SKBr3 (Breast carcinoma)(Bali et al., *Clin. Cancer Res*. 2005 Sep. 1; 11(17):6382-9); BT474 (Breast carcinoma)(Zhu X F, et al., *Cancer Sci*. 2006 January; 97(1):84-9).

The compounds of the invention are also potent, specific inhibitors of eukaryotic, especially mammalian, cell proliferation. Thus, in another aspect, the invention provides methods of inhibiting mammalian cell proliferation as a therapeutic approach towards the treatment or prevention of diseases characterized by unwanted or abnormal cell proliferation. In its broadest sense, the method involves only a single step— the administration of an effective amount of at least one pharmacologically active compound according to the invention to a mammalian cell in situ. The compound may act cytostatically, cytotoxically, or by a combination of both mechanisms to inhibit cell proliferation. Mammalian cells treatable in this manner include vascular smooth muscle cells, fibroblasts, endothelial cells, various pre-cancer cells and various cancer cells. In a preferred embodiment, cell proliferation is inhibited in a subject suffering from a disorder that is characterized by unwanted or abnormal cell proliferation. Such diseases are described more fully below.

Based in part on the surmised role of mammalian cell proliferation in certain diseases, the invention is also directed to methods of treating or preventing other diseases (in addition to cancer) characterized by abnormal cell proliferation. In the method, an effective amount of at least one compound according to the invention, or a pharmaceutical composition thereof, is administered to a patient suffering from a disorder that is characterized by abnormal cell proliferation.

Diseases which are characterized by abnormal cell proliferation that can be treated or prevented by means of the present invention include blood vessel proliferative disorders, fibrotic disorders, arteriosclerotic disorders and various cancers.

Blood vessel proliferation disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferative disorders include arthritis, where new capillary blood vessels invade the joint and destroy cartilage and ocular diseases such as diabetic retinopathy, where new capillaries in the retina invade the vitreous, bleed and cause blindness and neovascular glaucoma.

Another example of abnormal neovascularization is that associated with solid tumors. It is now established that unrestricted growth of tumors is dependent upon angiogenesis and that induction of angiogenesis by liberation of angiogenic factors can be an important step in carcinogenesis. For example, basic fibroblast growth factor (bFGF) is liberated by several cancer cells and plays a crucial role in cancer angiogenesis. The demonstration that certain animal tumors regress when angiogenesis is inhibited has provided the most compelling evidence for the role of angiogenesis in tumor growth. Other cancers that are associated with neovascularization include hemangioendotheliomas, hemangiomas and Kaposi's sarcoma.

Proliferation of endothelial and vascular smooth muscle cells is the main feature of neovascularization. The invention is useful in inhibiting such proliferation, and therefore in inhibiting or arresting altogether the progression of the angiogenic condition which depends in whole or in part upon such neovascularization. The invention is particularly useful when the condition has an additional element of endothelial or vascular smooth muscle cell proliferation that is not necessarily associated with neovascularization. For example, psoriasis may additionally involve endothelial cell proliferation that is independent of the endothelial cell proliferation associated with neovascularization. Likewise, a solid tumor which requires neovascularization for continued growth may also be a tumor of endothelial or vascular smooth muscle cells. In this case, growth of the tumor cells themselves, as well as the neovascularization, is inhibited by the compounds described herein.

The invention is also useful for the treatment of fibrotic disorders such as fibrosis and other medical complications of fibrosis which result in whole or in part from the proliferation of fibroblasts. Medical conditions involving fibrosis (other than atherosclerosis, discussed below) include undesirable tissue adhesion resulting from surgery or injury.

Other cell proliferative disorders which can be treated by means of the invention include arteriosclerotic conditions. Arteriosclerosis is a term used to describe a thickening and hardening of the arterial wall. An arteriosclerotic condition as used herein means classical atherosclerosis, accelerated atherosclerosis, atherosclerotic lesions and any other arteriosclerotic conditions characterized by undesirable endothelial and/or vascular smooth muscle cell proliferation, including vascular complications of diabetes.

Proliferation of vascular smooth muscle cells is a main pathological feature in classical atherosclerosis. It is believed that liberation of growth factors from endothelial cells stimulates the proliferation of subintimal smooth muscle which, in turn, reduces the caliber and finally obstructs the artery. The invention is useful in inhibiting such proliferation, and therefore in delaying the onset of, inhibiting the progression of, or even halting the progression of such proliferation and the associated atherosclerotic condition.

Proliferation of vascular smooth muscle cells produces accelerated atherosclerosis, which is the main reason for failure of heart transplants that are not rejected. This proliferation is also believed to be mediated by growth factors, and can ultimately result in obstruction of the coronary arteries. The invention is useful in inhibiting such obstruction and reducing the risk of, or even preventing, such failures.

Vascular injury can also result in endothelial and vascular smooth muscle cell proliferation. The injury can be caused by any number of traumatic events or interventions, including vascular surgery and balloon angioplasty. Restenosis is the main complication of successful balloon angioplasty of the coronary arteries. It is believed to be caused by the release of growth factors as a result of mechanical injury to the endothelial cells lining the coronary arteries. Thus, by inhibiting unwanted endothelial and smooth muscle cell proliferation, the compounds described herein can be used to delay, or even avoid, the onset of restenosis.

Other atherosclerotic conditions which can be treated or prevented by means of the present invention include diseases of the arterial walls that involve proliferation of endothelial and/or vascular smooth muscle cells, such as complications of diabetes, diabetic glomerulosclerosis and diabetic retinopathy.

The compounds described herein are also potent antineoplastic agents and are therefore useful in treating or preventing various types of neoplastic diseases. Neoplastic diseases which can be treated by means of the present invention include, but are not limited to, biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute and chronic lymphocytic and myelogenous leukemia, multiple myeloma, AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreatic cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma (teratomas, choriocarcinomas)), stromal tumors and germ cell tumors; thyroid cancer, including thyroid adenocarcinoma and medullar carcinoma; and renal cancer including adenocarcinoma and Wilms tumor.

The compounds of the invention are useful with hormone dependent and also with nonhormone dependent cancers. They also are useful with prostate and breast cancers. They further are useful with multidrug resistant strains of cancer.

In addition to the particular disorders enumerated above, the invention is also useful in treating or preventing dermatological diseases including keloids, hypertrophic scars, seborrheic dermatosis, papilloma virus infection (e.g., producing verruca vulgaris, verruca plantaris, verruca plan, condylomata, etc.), eczema and epithelial precancerous lesions such as actinic keratosis; other inflammatory diseases including proliferative glomerulonephritis; lupus erythematosus; scleroderma; temporal arthritis; thromboangiitis obliterans; mucocutaneous lymph node syndrome; and other pathologies mediated by growth factors including uterine leiomyomas.

Depending on the disease to be treated and the subject's condition, the compounds and compositions of the present invention may be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each route of administration. The present invention also contemplates administration of the compounds and compositions of the present invention in a depot formulation.

In the treatment or prevention of cancers, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

The compounds and compositions of the present invention can be combined with a second anticancer compound or composition.

The weight ratio of the compound of the present invention to the second anticancer compound or composition may be varied and will depend upon the effective dose of each ingredient. Generally, an effective dose of each will be used. Thus, for example, when a compound of the present invention is combined with an anticancer compound the weight ratio of the compound of the present invention to the anticancer compound will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

EXAMPLES

Reagents and solvents used below can be obtained from commercial sources such as Aldrich Chemical Co. (Milwaukee, Wis., USA). Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 µL was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

Compounds within the scope of this invention can be synthesized as described below, using a variety of reactions known to the skilled artisan. A sample of useful routes to both intermediates and compounds of formula (I) within this claim are provided below. In the descriptions of the syntheses that follow, some precursors were obtained from commercial sources.

Compounds of the invention can be prepared using conventional synthetic methodology. Examples of approaches that may be taken to synthesize these compounds are shown below. Nonetheless, one skilled in the art will recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are within the scope of the invention.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Compounds of the present invention (I) can be generally synthesized as set fourth in scheme 1. It should be understood that one of skill in the art could devise alternate routes to many of these intermediates. Similarly, a skilled artisan could devise alternate routes to the claimed analogs. The specific reaction route to a representative compounds (I) are shown in Schemes 2 and 3.

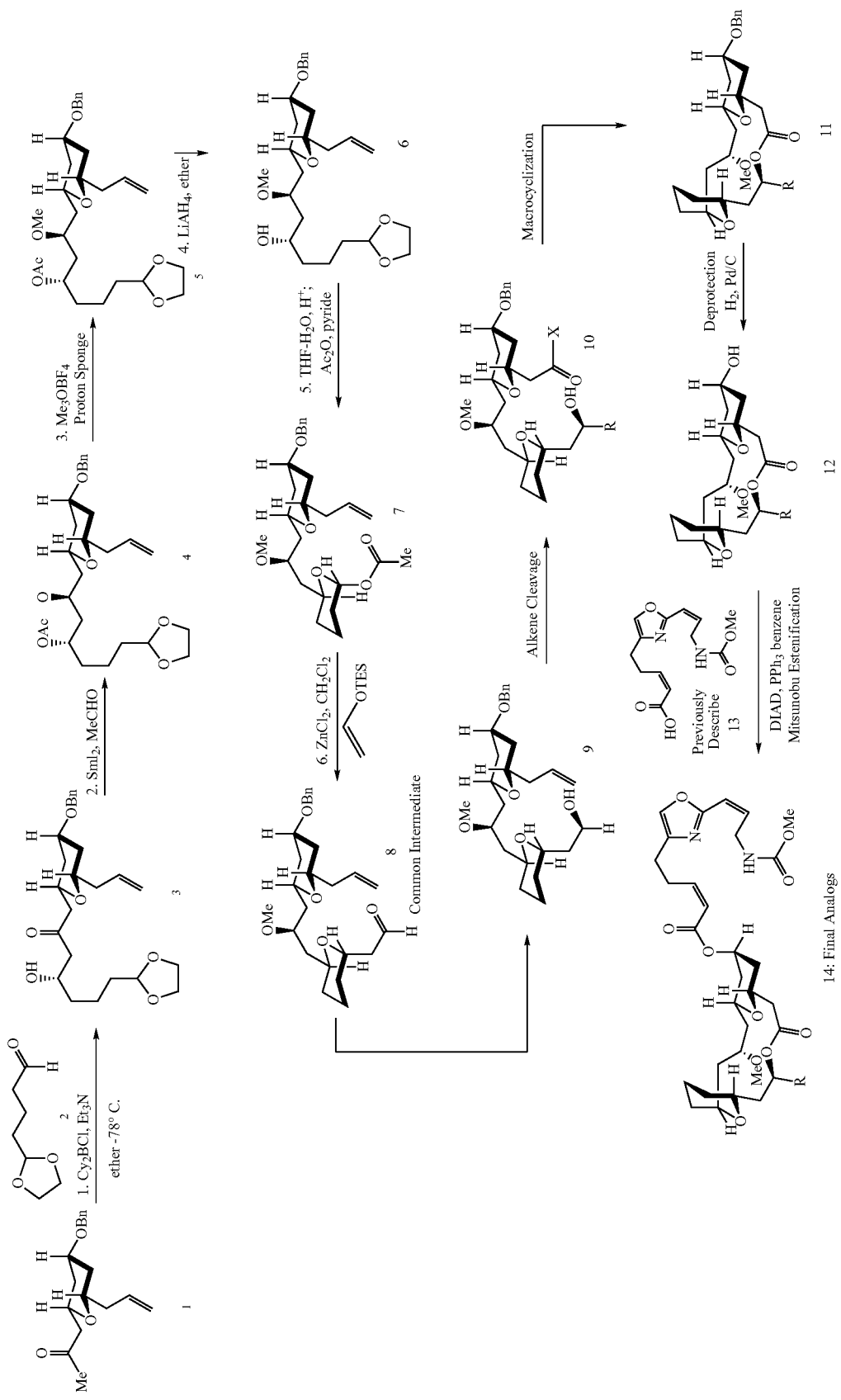
Scheme 1

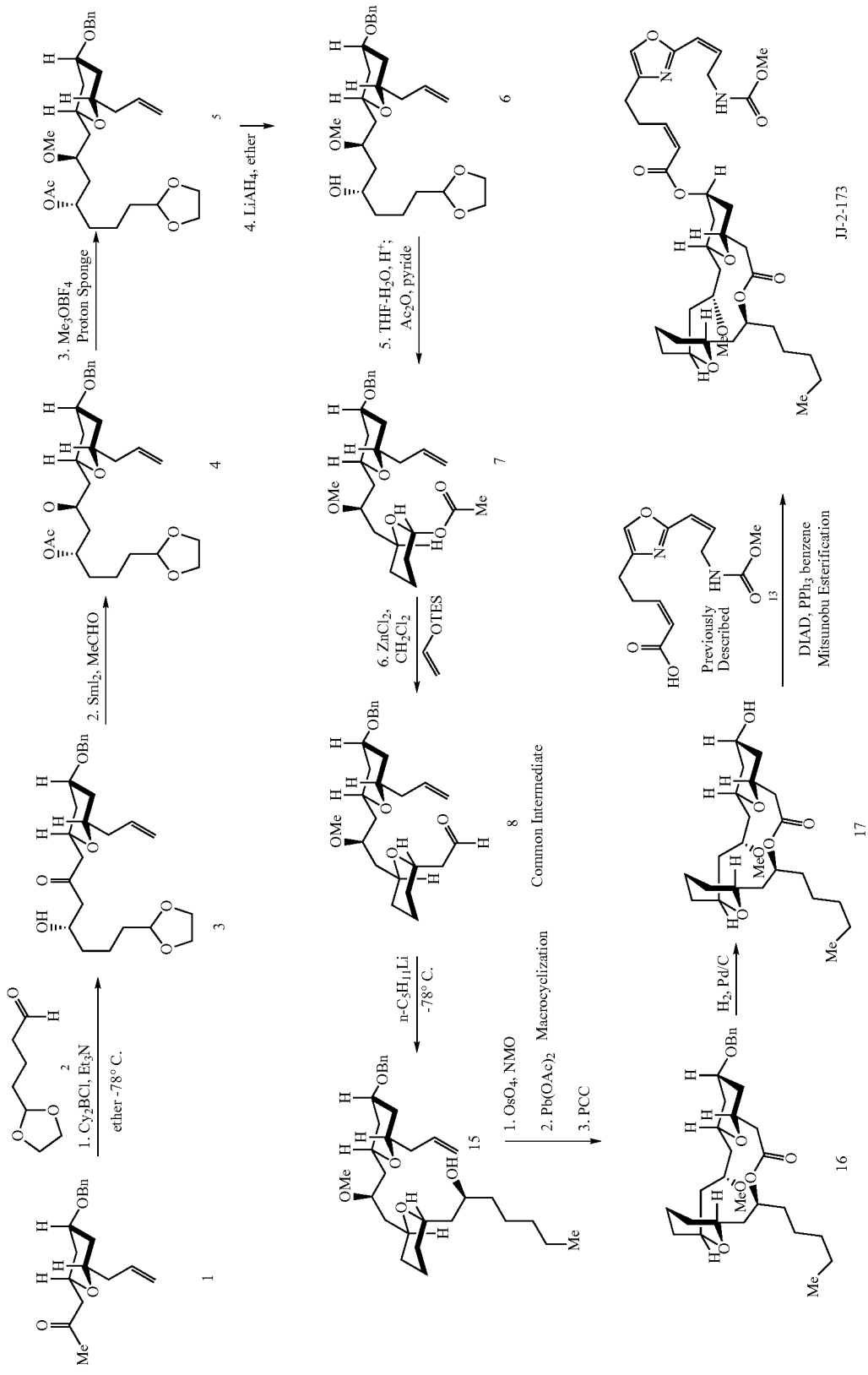

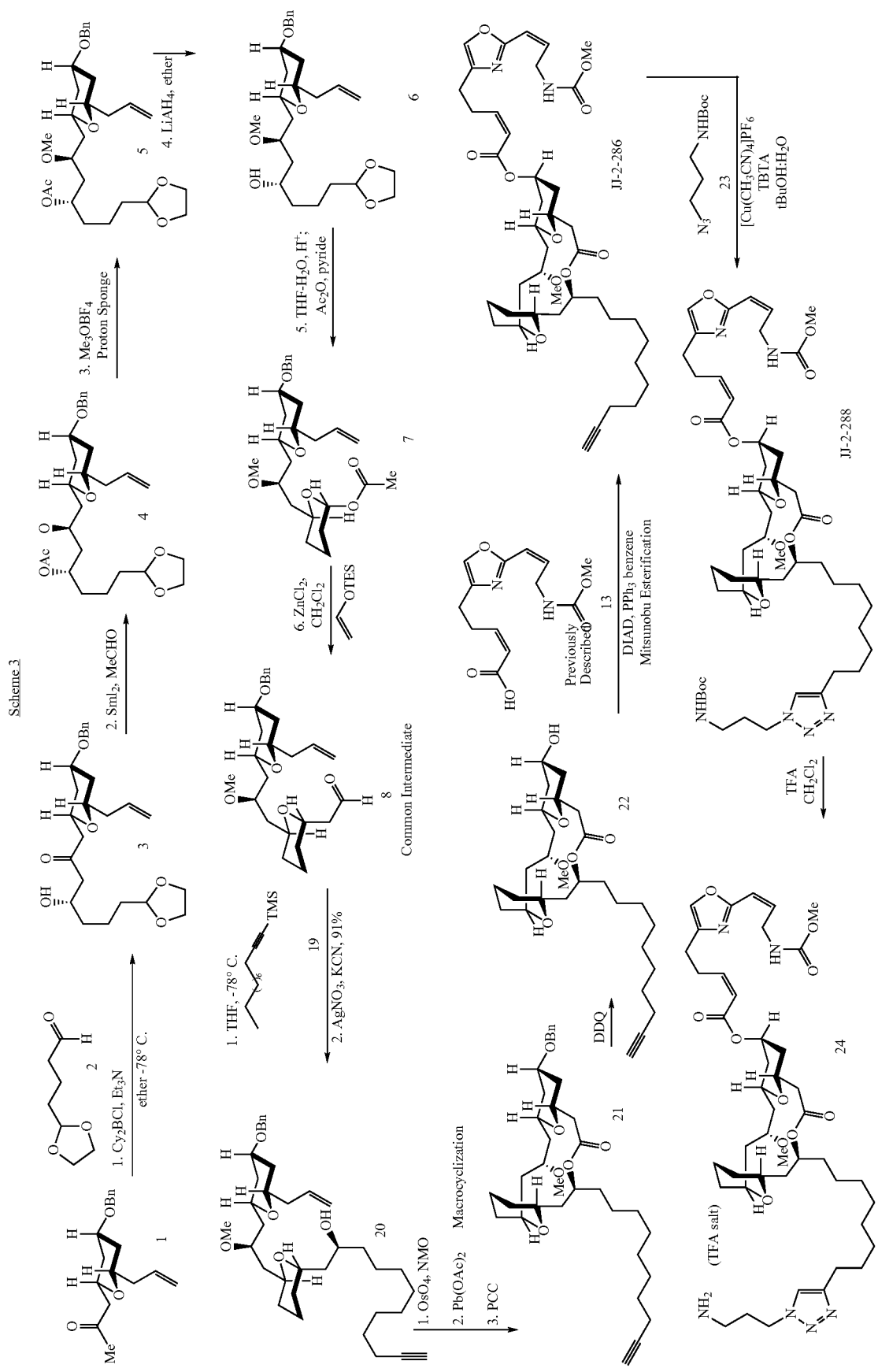
Scheme 3

Experimentals

Ketone 3. To ketone 1 (2.01 g, 6.98 mmol) in diethyl ether (100 mL) at 0° C., triethyl amine (1.68 mL, 12.04 mmol) was added followed by dicyclohexylboron chloride (10.47 mL of 1.0 M solution in hexane, 10.47 mmol). The resulting white suspension was stirred for 15 min at 0° C., and warmed up to ambient temperature for 15 min. Reaction mixture was cooled to −78° C., and treated with 5,5-ethylenedioxy-1-pentanal 2 (1.74 g, 12.04 mmol) in diethyl ether (20 mL) over a 10 min period. The reaction mixture was stirred for 5 h at −78° C., quenched by addition of 112 mL of methanol:pH 7 buffer (6:1). Upon warming to −20° C., 60 mL of methanol-30% hydrogen peroxide (2:1) was added. The stirring was continued for 12 h. The resulting colorless solution was partitioned between ethyl acetate (400 mL) and saturated aqueous solution of Na2SO3 (300 mL). The aqueous layer was extracted with ethyl acetate (2×50 mL). Organic layers were combined, dried over anhydrous MgSO4, filtered and concentrated in vacuo. Flash chromatography yielded 2.91 g of ketone 3 as colorless oil (96% yield). MS calculated for $C_{25}H_{36}O_6$ 432.3 (M+). Found 455.1 (M+Na).

Alcohol 4. A solution of ketone 3 (5.4 g, 12.5 mmol) and acetaldehyde (2.82 mL, 50 mmol) in THF (150 mL) was cooled to −10° C. and treated with SmI2 (35 mL, 0.1 M solution in THF, 3.5 mmol). The reaction mixture was stirred for 30 min, quenched by addition of saturated aqueous solution of NaHCO3 (100 mL), extracted with ethyl acetate (100 mL), dried over anhydrous MgSO4, filtered and concentrated in vacuo. Flash chromatography afforded 4.7 g of alcohol 4 as colorless oil (79% yield). MS calculated for $C_{27}H_{40}O_7$ 476.3 (M+). Found 499.1 (M+Na).

Methyl Ether 5. A solution of alcohol 4 (3.83 g, 8.04 mmol) and 1,8-Bis(dimethylamino)naphthalene (6.88 g, 32.2 mmol) in dichloromethane (160 mL) was cooled to 0° C. and treated with trimethyloxonium tetrafluoroborate (3.57 g, 24.12 mmol) followed by activated 4 Å molecular sieves. The reaction mixture was stirred for 2 h, quenched by addition of 2-propanol (40 mL). The mixture was diluted with diethyl ether (500 mL), and organic layers were extracted with aqueous solution of HCl (250 mL, 0.6 M), aqueous solution of NaHCO3 (300 mL) and brine (150 mL). Combined organic layers were dried over anhydrous MgSO4, filtered and concentrated in vacuo. Flash chromatography yielded 3.59 g of methyl ether 5 as a colorless oil (91% yield). MS calculated for $C_{28}H_{42}O_7$ 490.3 (M+). Found 513.2 (M+Na).

Alcohol 6. Lithium aluminum hydride (349 mg, 9.2 mmol) was suspended in diethyl ether (50 mL), cooled to −78° C., and treated with methyl ether 5 (2.65 g, 5.4 mmol) in diethyl ether (35 mL) over a 10 min period. The reaction mixture was warmed to 0° C. and stirred for 1 h, quenched by dropwise addition of water (0.3 mL). The resulting suspension was allowed to reach ambient temperature, vigorously stirred for 12 h, diluted with diethyl ether (50 mL), dried with anhydrous MgSO4, filtered and concentrated in vacuo. Flash chromatography yielded 2.25 g of alcohol 6 as a colorless oil (93% yield). MS calculated for $C_{26}H_{40}O_6$ 448.3 (M+). Found 471.1 (M+Na).

Acetate 7. A solution of alcohol 6 (110 mg, 0.25 mmol) in THF:H2O (2.5:0.4 mL), was treated with catalytic amount of concentrated H2SO4. The resulting solution was gently refluxed for 6 h, diluted with diethyl ether (10 mL), washed with saturated aqueous solution of NaHCO3 (10 mL), and brine (10 mL). Combined organic layers were dried over anhydrous MgSO4, filtered, concentrated in vacuo, and dissolved in dichloromethane (5 mL). The resulting solution was treated with acetic anhydride (130 μL, 1.40 mmol), pyridine (99 μL, 1.22 mmol), and 4-Dimethylaminopyridine (33 mg, 0.27 mmol). After 30 min at ambient temperature, the reaction mixture was diluted with diethyl ether (20 mL) and washed with saturated aqueous solution of NaHCO3 (10 mL), and brine (10 mL). Organic layer was dried with anhydrous MgSO4, filtered and concentrated in vacuo. Flash chromatography yielded 94 mg of acetate 7 as a colorless oil (86% yield). MS calculated for $C_{26}H_{38}O_6$ 446.3 (M+). Found 387.1 (M-OAc).

Aldehyde 8. A solution of acetate 7 (80 mg, 0.17 mmol) and triethylvinyloxysilane (57 mg, 0.31 mmol) in dichloromethane (6 mL) was cooled to −78° C. and treated with zinc chloride (310 μL, 1 M solution in diethyl ether, 0.31 mmol). Reaction mixture was warmed to ambient temperature, quenched with saturated aqueous solution of NaHCO3 (3 mL.) Aqueous layer was extracted with diethyl ether (3×5 mL), dried with anhydrous MgSO4, filtered and concentrated in vacuo. Flash chromatography yielded 48 mg of aldehyde 8 as a colorless oil (64% yield). MS calculated for $C_{26}H_{38}O_5$ 430.3 (M+). Found 431.2 (M+1).

Alcohol 15. A solution of aldehyde 8 (60 mg, 0.14 mmol) in THF (2 mL) was cooled to −78° C. and treated with pentylmagnesium bromide (140 μL, 2 M solution in diethyl ether, 0.28 mmol). Reaction mixture was allowed to warm to 0° C., quenched with saturated aqueous solution of NH4Cl (1 mL), and extracted with ethyl acetate (2×2 mL). Organic layers were dried with anhydrous Na2SO4, and concentrated in vacuo. Flash chromatography yielded 53 mg of alcohol 15 as a mixture 1:1.2 anti:syn as a colorless oil (76% yield). MS calculated for $C_{31}H_{50}O_5$ 502.4 (M+). Found 503.2 (M+1).

Lactone 16. A solution of alcohol 15 (75 mg, 0.15 mmol) and 4-methylmorpholine N-oxide (35 mg, 0.30 mmol) in t-BuOH:THF:H2O (1.8:2:0.4 mL) was treated with Osmium tetroxide (70 μL, 2.5 wt % in t-BuOH) at ambient temperature for 2 h. After 2 h, solid Na2S2O3 and Na2SO4 were added to the reaction mixture and further stirred for 15 min. The reaction mixture was decanted and solids were washed with ethyl acetate (4×5 mL), and concentrated in vacuo. Flash chromatography afforded 63 mg of triol as a colorless oil (78% yield). MS calculated for $C_{31}H_{52}O_7$ 536.4 (M+) .Found 537.3 (M+1).

A solution of triol (60 mg, 0.11 mmol) in ethyl acetate (3 mL) was treated with lead tetraacetate (90 mg, 0.20 mmol) at 0° C. After 30 min, the reaction mixture was passed through a plug of silica gel and concentrated in vacuo. The resulting colorless oil was left for 12 h at ambient temperature to yield 32 mg of lactol as a colorless oil (56% yield) and 8 mg of hydroxy aldehyde (15% yield). MS calculated for $C_{30}H_{48}O_6$ 504.4 (M+). Found 539.2 (M+Cl).

A solution containing lactol (23 mg, 0.046 mmol) in dichloromethane (1 mL) at 0° C. was treated with pyridinium chloride (39 mg, 0.18 mmol) and activated 4 Å molecular sieves. The reaction mixture was stirred overnight at ambient temperature. Crude product was concentrated in vacuo and purified by flash chromatography to afford 23 mg of lactone 16 as a white solid (70% yield). MS calculated for $C_{30}H_{46}O_6$ 502.3 (M+). Found 503.1 (M+1).

Macrolide 17. A solution of lactone 16 (31 mg, 0.062 mmol) in methanol (1 mL) was treated with Palladium (6.5 mg, 10 wt % on activated Carbon, 6.2 μmol). The reaction mixture was charged with hydrogen gas using a balloon, stirred for 3 h, filtered through Celite, and concentrated in vacuo to yield 25 mg of macrolide 17 as a white solid (99% yield). MS calculated for $C_{23}H_{40}O_6$ 412.3 (M+). Found 413.1 (M+1).

(±)-JJ-2-173. A solution containing macrolide 17 (21 mg, 0.051 mmol), acid 13 (43 mg, 0.15 mmol) and triphenylphosphine (44 mg, 0.17 mmol) in anhydrous benzene (2.5 mL) was treated with diisopropyl azodicarboxylate (33 μL, 0.17 mmol) at ambient temperature. After 10 min, reaction mixture was concentrated in vacuo. Flash chromatography yielded 26 mg of pentyl analog 18 as a white solid (76% yield). MS calculated for $C_{36}H_{54}N_2O_{10}$ 674.4 (M+). Found 675.2 (M+1).

The following analogs were prepared according to a general synthetic sequence used for the synthesis of (±)-JJ-2-173.

(+)JJ-2-37 and (−)JJ-2-37: $^1$H NMR (500 MHz, CDCl$_3$) δ 7.37 (s, 1H), 6.31 (m, 2H), 6.07 (m, 1H), 5.88 (d, 1H, J=11.5 Hz), 5.66 (m, 1H), 5.54 (br s, 1H), 5.33 (d, 2H, J=12.5 Hz), 5.22 (t, 1H), 4.23 (br s, 2H), 4.22 (m, 1H), 3.99 (t, 1H, J=11 Hz), 3.65 (s, 3H), 3.52 (m, 3H), 3.32 (s, 3H), 3.01 (dd, 2H, J=7.5Hz), 2.70 (t, 2H, J=7 Hz), 2.51 (dd, 1H, J=13, 3.5 Hz), 2.32 (m, 2H), 1.79-1.94 (m, 4H), 1.69-1.78 (m, 2H), 1.48-1.60 (m, 7H), 1.35 (m, 1H), 1.15-1.28 (m, 4H), 0.91 (m, 1H), 0.85 (dd, 6H, J=6.5, 1.5 Hz). HPLC separation of (+)JJ-2-37 and (−)JJ-2-37: column analytical AD-H chiral, flow 1 mL/min, elution with 15:1 Hex:2-propanol, elution time for (+)JJ-2-37 36.2 min, elution time for (−)JJ-2-37 46.8 min (±)-JJ-2-96
$^1$H NMR (500 MHz, CDCl$_3$) δ 7.37 (s, 1H), 6.31 (m, 2H), 6.08 (m, 1H), 5.87 (d, 1H, J=11.5 Hz), 5.50 (br s, 1H), 5.23 (t, 1H), 4.96 (m, 1H), 4.30 (br s, 2H), 4.22 (m, 1H), 3.98 (t, 1H), 3.66 (s, 3H), 3.53 (m, 3H), 3.34 (s, 3H), 3.02 (dd, 2H, J=7 Hz), 2.71 (t, 2H, J=7.5 Hz), 2.52 (dd, 1H, J=13,4 Hz), 2.33 (m, 2H), 1.93 (t, 1H, J=11.5 Hz), 1.76-1.87 (m, 2H), 1.47-1.70 (m, 6H), 1.18-1.36 (m, 10H), 1.11 (m, 2H), 0.92 (m, 1H), 0.82 (d, 6H, J=7 Hz)

(±)-JJ-2-194
$^1$H NMR (500 MHz, CDCl$_3$) δ 7.38 (s, 1H), 6.31 (m, 2H), 6.10 (m, 1H), 5.88 (d, 1H, J=11.4 Hz), 5.48 (br s, 1H), 5.23 (t, 1H), 4.96 (m, 1H), 4.31 (br s, 2H), 4.22 (m, 1H), 3.99 (t, 1H), 3.67 (s, 3H), 3.60 (t, 2H, J=6.6 Hz) 3.52 (m, 3H), 3.33 (s, 3H), 3.03 (dd, 2H), 2.72 (t, 2H), 2.52 (dd, 1H), 2.32 (m, 3H), 1.54-1.95 (m, 11H), 1.23-1.34 (m, 10H), 0.89 (m,2H)

Alcohol 15. Magnesium turnings (80 mg, 3.34 mmol) and 1,2-dibromoethane (20 μL) were heated for 3 min with a heat gun. A solution 10-trimethylsilyl-1-bromodecyne 19 (364 mg, 1.26 mmol) in THF (6 mL) was added and heated to 45° C. for 3 h. The reaction was cooled to −78° C. and solution of aldehyde 8 (229 mg, 0.53 mmol) in THF (6.6 mL) was added over a 10 min period. Reaction mixture was allowed to warm to 0° C., quenched with saturated aqueous solution of NH$_4$Cl (3 mL), and extracted with ethyl acetate (4×5 mL). Organic layers were dried with anhydrous MgSO$_4$, filtered and concentrated in vacuo. Flash chromatography yielded 223 mg of trimethylsilyl-ynol as a mixture 1.1:1 anti:syn as a colorless oil (65% yield). MS calculated for C$_{39}$H$_{64}$O$_5$Si 640.5 (M+). Found 641.3 (M+1).

A solution of trimethylsilyl-ynol (105 mg, 0.16 mmol) in ethanol (6 mL) was treated with solution of Silver nitrate (111 mg, 0.66 mmol) in ethanol:H$_2$O (1.2:0.3 mL) at 0° C. over a period of 5 min. After 15 minutes, a solution of potassium cyanide (213 mg, 3.28 mmol) in H$_2$O (1.5 mL) was added and the reaction was stirred for another 15 min at 0° C. Reaction mixture was allowed to warm to ambient temperature and stirred for 10 min, concentrated in vacuo. Flash chromatography afforded 85 mg of alcohol 20 as a colorless oil (91% yield). MS calculated C$_{36}$H$_{56}$O$_5$ 568.4 (M+). Found 569.3 (M+1).

Lactone 21. A solution of alcohol 20 (80 mg, 0.14 mmol) and 4-methylmorpholine N-oxide (33 mg, 0.28 mmol) in t-BuOH:THF:H$_2$O (0.9:1:0.2 mL) was treated with Osmium tetroxide (60 μL, 2.5 wt % in t-BuOH) at ambient temperature for 1.5 h. After 1.5 h, solid Na$_2$S$_2$O$_3$ was added to the reaction mixture and further stirred for 15 min. The reaction mixture was concentrated in vacuo, and flash chromatography afforded 72 mg of triol as a colorless oil (86% yield). MS calculated for C$_{36}$H$_{58}$O$_7$ 602.4 (M+). Found 603.3 (M+1).

A solution of triol (69 mg, 0.11 mmol) in ethyl acetate (3 ML) was treated with lead tetraacetate (91 mg, 0.21 mmol) at −10° C. After 30 min, the reaction mixture was passed through a plug of silica gel and concentrated in vacuo. The resulting colorless oil was left for 12 h at ambient temperature to yield 22 mg of lactol as a white solid (34% yield) and 27 mg of hydroxy aldehyde (42% yield). MS calculated for C$_{35}$H$_{54}$O$_6$ 570.4 (M+). Found 570.3 (M+).

A solution containing lactol (19 mg, 0.033 mmol) in dichloromethane (1 mL) at −10° C. was treated with pyridinium chloride (29 mg, 0.13 mmol) and activated 4 Å molecular sieves. The reaction mixture was stirred for 1 h at ambient temperature. Crude product was concentrated in vacuo and purified by flash chromatography to afford 12 mg of lactone 21 as a white solid (62% yield). $^1$H NMR (500 MHz, CDCl$_3$) δ 7.26-7.35 (m, 5H), 4.95 (t, 1H, J=10 Hz), 4.56 (s, 1H), 4.19 (dd, 1H, J=11.5, 4.5 Hz), 3.65 (t, 1H, J=13 Hz), 3.59 (m, 1H), 3.45 (m, 2H), 3.33 (s, 3H), 3.12 (t, 1H, J=11.5 Hz), 2.53 (dd, 1H, J=9, 4 Hz), 2.30-2.41 (m, 2H), 2.15 (dt, 2H, J=7, 2.5 Hz), 1.95-2.06 (m, 3H), 1.91 (t, 1H, J=2.5), 1.80 (m, 1H), 1.45-1.63 (m, 5H), 1.31-1.35 (m, 5H), 1.18-1.29 (m, 15H), 0.89 (t, 1H, J=12 Hz)

Macrolide 22. A solution of lactone 21 (17 mg, 0.03 mmol) in dichloromethane (2 mL) and pH 7 buffer (0.2 mL) was treated with 2,3-Dichloro-5,6-dicyano-p-benzoquinone (69 mg, 0.30 mmol) at ambient temperature. After 20 h of vigorous stirring, the reaction mixture was concentrated in vacuo. Flash chromatography yielded 13 mg of macrolide 22 as a white solid (90% yield). MS calculated for C$_{28}$H$_{46}$O$_6$ 478.3 (M+). Found 479.1 (M+1).

(±)-JJ-2-286.

A solution containing macrolide 22 (12 mg, 0.025 mmol), acid 13 (15 mg, 0.053 mmol) and triphenylphosphine (21 mg, 0.079 mmol) in anhydrous benzene (1.3 mL) was treated with diisopropyl azodicarboxylate (16 μL, 0.079 mmol) at ambient temperature. After 15 min, reaction mixture was concentrated in vacuo. Flash chromatography yielded 12.4 mg of pentyl analog 23 as a white solid (67% yield). MS calculated for C$_{41}$H$_{60}$N$_2$O$_{10}$ 740.4 (M+). Found 741.2 (M+1).

(±)-JJ-2-288. Alkynyl analog JJ-2-286 (1.8 mg, 2.4 μmol), (3-azido-propyl)-carbamic acid t-butyl ester 23 (1.5 mg, 7.3 μmol) and tris-(benzyltriazolylmethyl)amine (0.2 mg, 0.31 μmol) was dissolved in tBuOH:H$_2$O (0.8:0.4 mL). Catalytic amount of Tetrakis(acetonitrile)copper(I) hexafluorophosphate was added, and the reaction mixture was allowed to stir for 24 h at ambient temperature. Flash chromatography yielded 1.9 mg of triazole analog 25 as a white solid (86% yield). MS calculated for C$_{49}$H$_{76}$N$_6$O$_{12}$ 940.5 (M+). Found 941.1 (M+1).

Amine 24. A solution of triazole analog JJ-2-288 (2.4 mg, 2.5 μmol) in dichloromethane (0.5 mL) was treated with trifluoroacetic acid (50 μL). After 30 minutes, reaction mixture was concentrated in vacuo to yield 2 mg of amine 24 (95% yield), which was determined to be pure by thin layer chromatography.

Cell Growth/Viability Assays. All assays were performed using at least three replicate wells for each compound concentration tested. Cells were seeded in 96-well white plates at the density of 1000 cells/well in 100 μL of the appropriate cell culture media. Adherent A549, PC3 and HCT116 cells were allowed to attach and grow for 24 h and then treated with 30 μL of the solution of a compound and incubated further for 48 h. After incubation, cell viability was determined using a luminescence-based commercial kit (CellTiter-Glo, Promega) and luminescence was analyzed using a Wallac Victor III plate reader. Compound concentration that gave 50% reduction in cell viability when compared with untreated control cells was calculated from sigmoidal plots of cell viability versus drug concentration. To measure cell growth inhibition, similar viability assays were performed twice: at 0 h and after 48 h incubation. And then change in number of viable cells was measured and calculated from sigmoidal plots.

Biological Activity—Using methods similar to that described above, the following compounds were tested. Active compounds (compounds with activity equal to or greater than about 1-10 nM) are shown in Table 1. Inactive compounds (compounds with activity less than about 1 nM) are shown in Table 2.

TABLE 1

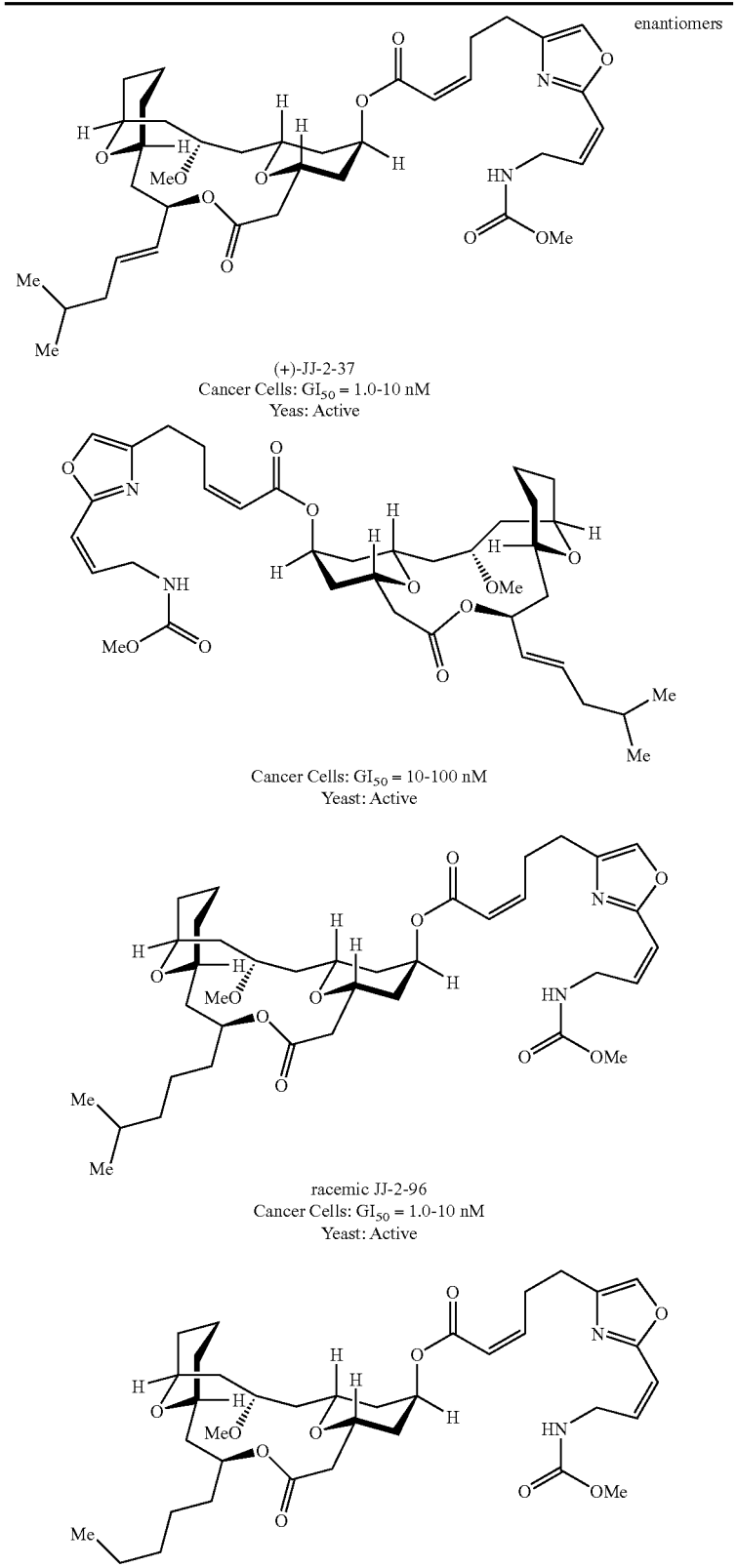

(+)-JJ-2-37
Cancer Cells: $GI_{50}$ = 1.0-10 nM
Yeas: Active

Cancer Cells: $GI_{50}$ = 10-100 nM
Yeast: Active racemic JJ-2-96
Cancer Cells: $GI_{50}$ = 1.0-10 nM
Yeast: Active TABLE 1-continued
racemic JJ-2-173
Cancer Cells: GI$_{50}$ =1.0-10 nM
Yeast: Active
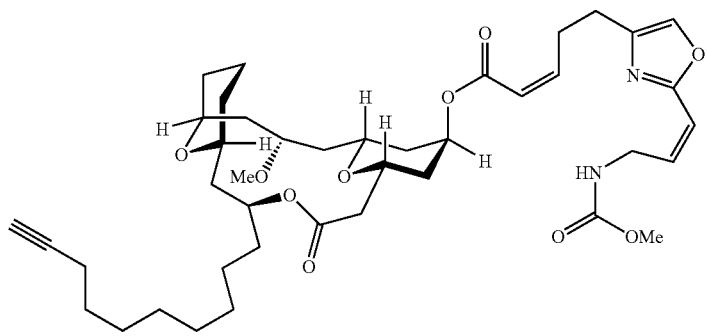
racemic JJ-2-286
Cancer Cells: GI$_{50}$ = 1.0-10 nM
Yeast: Active
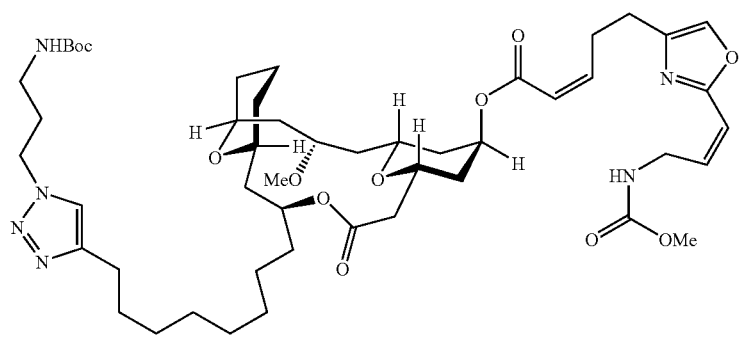
racemic JJ-2-288
Cancer Cells: GI$_{50}$ = 10-100 nM
Yeast: Active
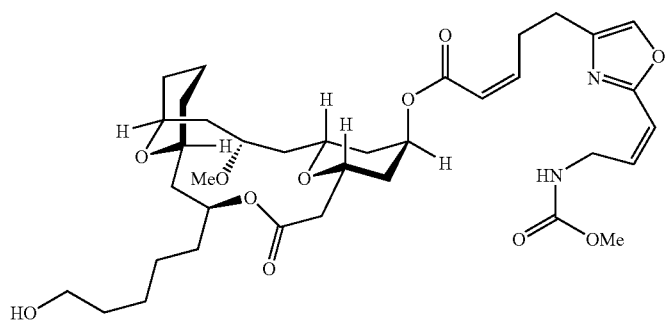
racemic JJ-2-194
Cancer Cells: GI$_{50}$ = 10-100 nM
Yeast: Inactive TABLE 2
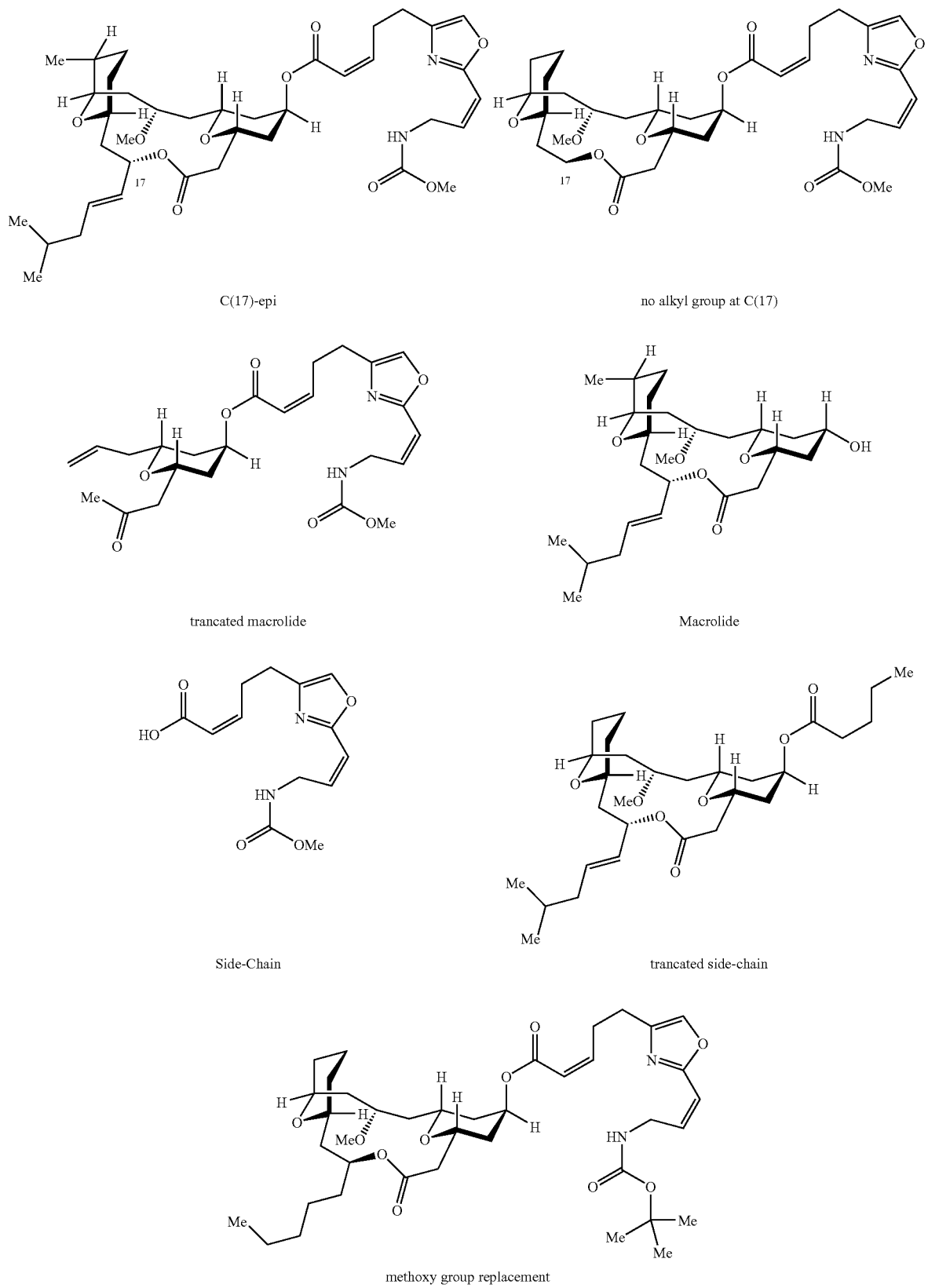

TABLE 2-continued

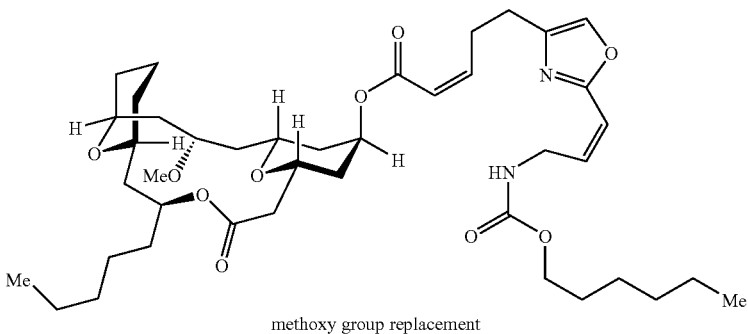
methoxy group replacement

The invention claimed is:

1. A compound of the formula (I) or a salt, enantiomer or racemate thereof:

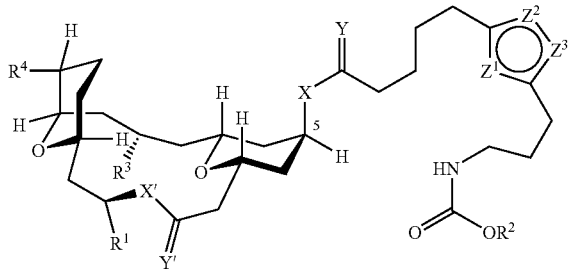

wherein:
  $R^1$ is —($C_{0-15}$ alkylene)-L-($C_{0-15}$ alkylene)-$Z^4$
    wherein each alkylene group in $R^1$ independently contains from 0 to 3 double or triple bonds; and wherein each alkylene group of $R^1$ may be unsubstituted or substituted;
  L is a bond, substituted or unsubstituted heterocyclyl, substituted or unsubstituted aryl, substituted or unsubstituted heteroaryl, —($CH_2CH_2O$)$_a$—, —$CONR^i$—, —$NR^iCO$—, —C(O)—, —S—, —S(O)— or —S(O)$_2$—;
  $Z^4$ is hydrogen, —$NR^iR^{vi}$, —$OR^{vi}$, —$SR^{vi}$, or —$CONR^iR^{vi}$;
  $R^2$ is $C_{1-3}$ alkyl;
  $R^3$ is hydrogen, $C_{1-6}$ alkyl, —$OR^i$, —$SR^i$, or —O(CO)$R^i$;
  $R^4$ is hydrogen or $C_{1-6}$ alkyl;
  each X and X' are independently O or $NR^i$;
  each Y and Y' are independently O or S;
  each of $Z^1$, $Z^2$, and $Z^3$, is independently selected from $CR^i$, N, O or S;
  the alkylene groups within the substituent on C5 may independently contain from 1 to 2 double bonds;
  a is an integer from 1-10;
  each $R^i$ is independently hydrogen or $C_{1-6}$ alkyl; and
  $R^{vi}$ is hydrogen, $C_{1-6}$ alkyl, or a label;
  provided that if X, X', Y, and Y' are O, $R^2$ is methyl, $R^3$ is methyl, and $R^4$ is methyl or hydrogen, then $R^1$ is not —CH=CHCH$_2$CH(CH$_3$)$_2$, CH$_2$CH$_2$CH$_2$CH(CH$_3$)$_2$, C≡CCH$_2$CH(CH$_3$)$_2$, —CH$_3$ or —H.

2. The compound of claim 1, wherein at least one alkylene group of $R^1$ is substituted with from 1 to 3 substituents selected from alkyl, halogen, —$NR^iR^{ii}$, —$OR^i$, —$SR^i$, —CN, —$NO_2$, =O, —OC(O)$R^i$, —C(O)$R^i$, —C(O)$NR^iR^{ii}$, —OC(O)$NR^iR^{ii}$, —$NR^{ii}C(O)R^i$, —$NR^iC(O)NR^{iii}R^{ii}$, —$CO_2R^i$, —$NR^iR^{ii}$, —$NR^{ii}CO_2R^i$, —$SR^i$, —S(O)$R^i$, —S(O)$_2R^i$, —S(O)$_2NR^iR^{ii}$, —$NR^iS(O)_2R^{ii}$, unsubstituted or substituted aryl, unsubstituted or substituted heteroaryl, and unsubstituted or substituted heterocyclyl, wherein each $R^i$, $R^{ii}$ and $R^{iii}$ are independently hydrogen or $C_{1-6}$ alkyl.

3. The compound of claim 1, which is of the formula (II):

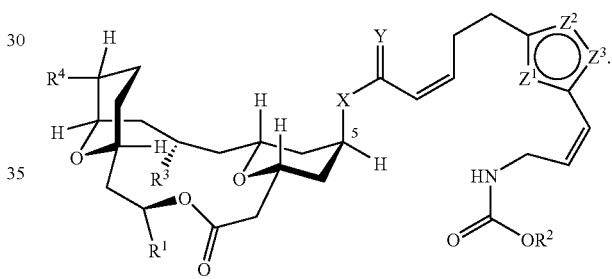

4. The compound of claim 1, wherein $Z^1$ is N, $Z^2$ is CH, and $Z^3$ is O.

5. The compound of claim 1, wherein X is O.

6. The compound of claim 1, wherein Y is O.

7. The compound of claim 1, wherein L is a bond, substituted or unsubstituted 5- or 6-membered heterocyclyl, substituted or unsubstituted phenyl, or substituted or unsubstituted 5- or 6-membered heteroaryl.

8. The compound of claim 1, wherein $Z^4$ is —$NR^iR^{vi}$.

9. The compound of claim 1, where $R^{vi}$ is an affinity label or fluorescent marker.

10. The compound of claim 1, where $R^3$ is $OR^i$.

11. The compound of claim 1, where $R^4$ is hydrogen or methyl.

12. The compound of claim 1, wherein $R^1$ is —$C_{1-15}$ alkynyl.

13. The compound of claim 1, wherein $R^1$ is —($C_{1-8}$ alkylene)-L-($C_{1-6}$ alkylene)-$Z^4$.

14. The compound of claim 1, wherein $R^1$ is —($C_{1-8}$ alkylene)-L-($C_{1-6}$ alkylene)-$NR^iR^{ii}$, where L is a unsubstituted or substituted 5- or 6-membered heterocyclyl, unsubstituted or substituted 5- or 6-membered heteroaryl, or unsubstituted or substituted phenyl.

15. The compound of claim 1, which is selected from the group consisting of:

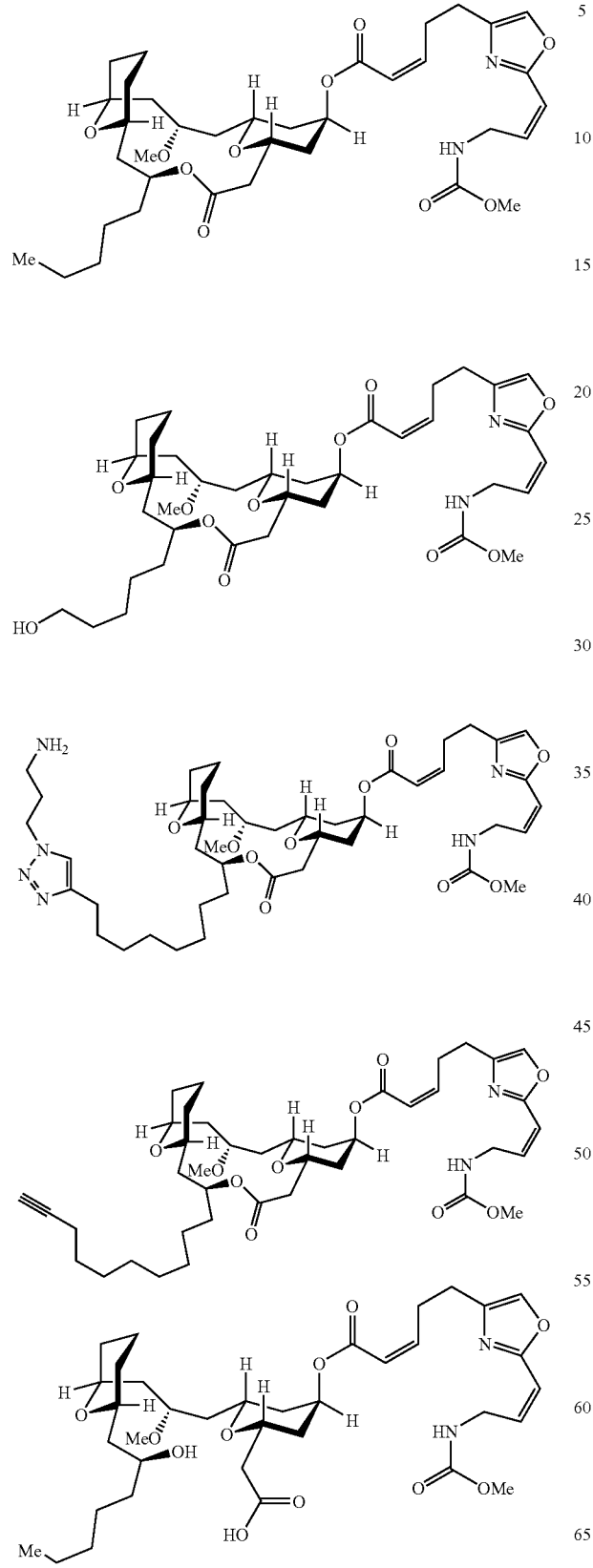

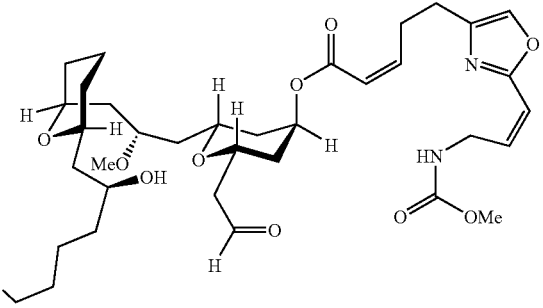

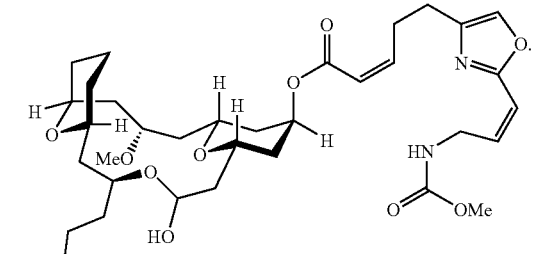

16. A compound of the formula (III) or a salt, enantiomer or racemate thereof:

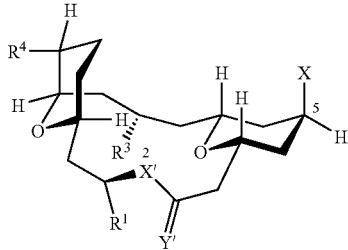

wherein

R$^1$ is —(C$_{0-15}$ alkylene)-L-(C$_{0-15}$ alkylene)-Z$^4$ wherein each alkylene group in R$^1$ independently contains from 0 to 3 double or triple bonds; and wherein each alkylene group of R$^1$ may be unsubstituted or substituted;

L is a bond, substituted or unsubstituted heterocyclyl, substituted or unsubstituted aryl, substituted or unsubstituted heteroaryl, —CONR$^i$—, —NR$^i$CO—, —C(O)—, —S—, —S(O)— or —S(O)$_2$—;

Z$^4$ is hydrogen, —NR$^i$R$^{ii}$, —OR$^i$, —SR$^i$, or —CONR$^i$R$^{ii}$;

R$^3$ is hydrogen, C$_{1-6}$ alkyl, —OR$^i$, —SR$^i$, or —O(CO)R$^i$;

R$^4$ is hydrogen or C$_{1-6}$ alkyl;

X is OR$^{iii}$;

X' is O or NR$^i$;

Y' is O or S;

each R$^i$ and R$^{ii}$ are independently hydrogen or C$_{1-6}$ alkyl; and

R$^{iii}$ is a hydroxy-protecting group, provided that if X, X', Y, and Y' are O, R$^2$ is methyl, R$^3$ is methyl, and R$^4$ is methyl or hydrogen, then R$^1$ is not —CH═CHCH$_2$CH(CH$_3$)$_2$, CH$_2$CH$_2$CH$_2$CH(CH$_3$)$_2$, C≡CCH$_2$CH(CH$_3$)$_2$, —CH$_3$ or —H.

17. The compound of claim 16, which is selected from the group consisting of:
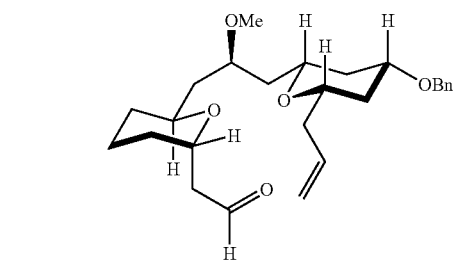
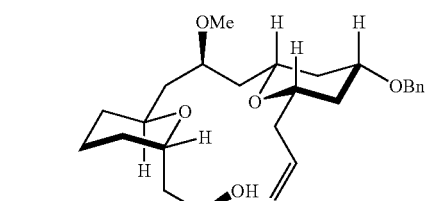
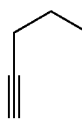
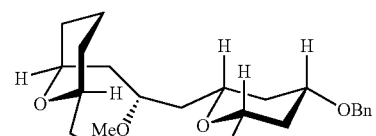
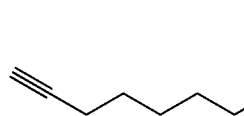
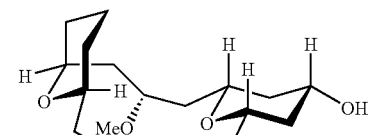
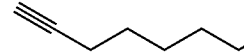
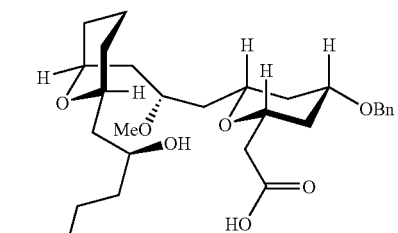
-continued
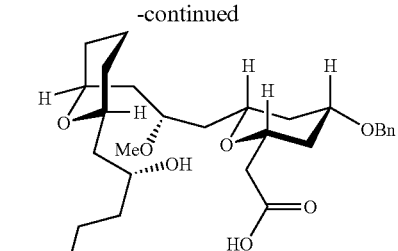
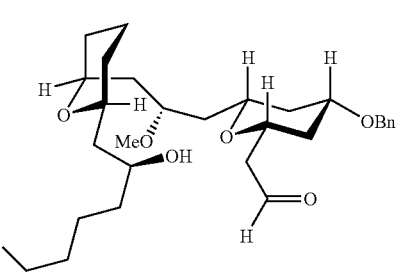
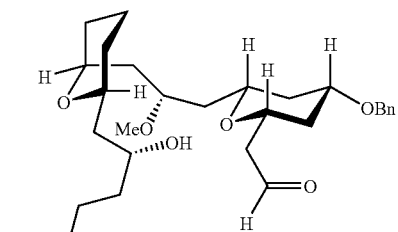
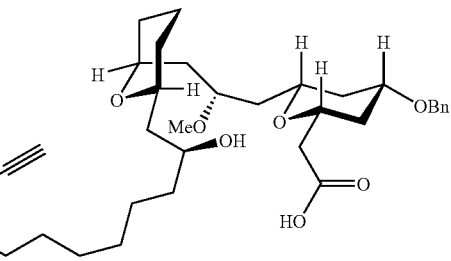
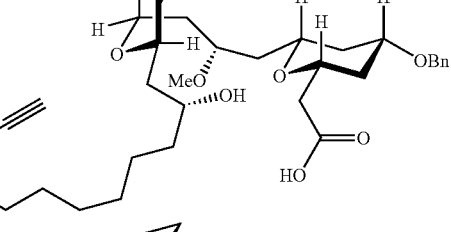
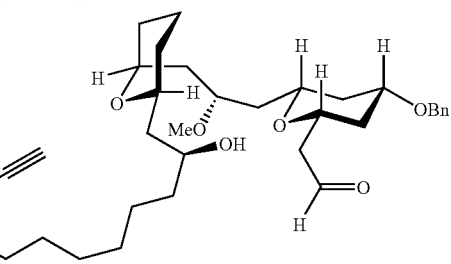

-continued

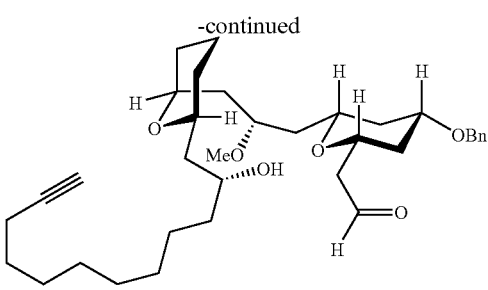

or a salt, enantiomer or racemate thereof.

18. A composition comprising a pharmaceutically acceptable carrier and the compound of the formula (I):

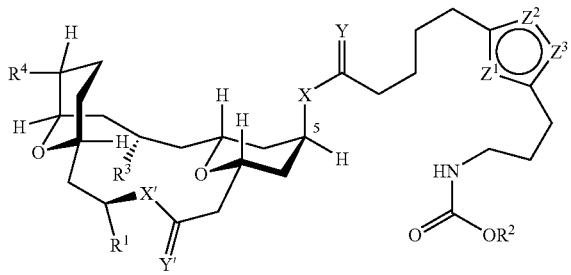

wherein:

$R^1$ is —($C_{0-15}$ alkylene)-L-($C_{0-15}$ alkylene)-$Z^4$
  wherein each alkylene group in $R^1$ independently contains from 0 to 3 double or triple bonds; and wherein each alkylene group of $R^1$ may be unsubstituted or substituted;

L is a bond, substituted or unsubstituted heterocyclyl, substituted or unsubstituted aryl, substituted or unsubstituted heteroaryl, —(CH$_2$CH$_2$O)$_a$—, —CONR$^i$—, —NR$^i$CO—, —C(O)—, —S—, —S(O)— or —S(O)$_2$—;

$Z^4$ is hydrogen, —NR$^i$R$^{vi}$, —OR$^{vi}$, —SR$^{vi}$, or —CONR$^i$R$^{vi}$;

$R^2$ is $C_{1-3}$ alkyl;

$R^3$ is hydrogen, $C_{1-6}$ alkyl, —OR$^i$, —SR$^i$, or —O(CO)R$^i$;

$R^4$ is hydrogen or $C_{1-6}$ alkyl;

each X and X' are independently O or NR$^i$;

each Y and Y' are independently O or S;

each of $Z^1$, $Z^2$, and $Z^3$, is independently selected from CR$^i$, N, O or S;

the alkylene groups within the substituent on C5 may independently contain from 1 to 2 double bonds;

a is an integer from 1-10;

each R$^i$ and R$^{ii}$ are independently hydrogen or $C_{1-6}$ alkyl; and

R$^{vi}$ is hydrogen, $C_{1-6}$ alkyl, or a label.

* * * * *

UNITED STATES PATENT AND TRADEMARK OFFICE
CERTIFICATE OF CORRECTION

PATENT NO. : 7,569,594 B2  
APPLICATION NO. : 11/348839  
DATED : August 4, 2009  
INVENTOR(S) : Kozmin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 656 days.

Signed and Sealed this

Seventh Day of September, 2010

David J. Kappos
*Director of the United States Patent and Trademark Office*